US00PP09501P

United States Patent [19]

Schrama

[11] Patent Number: Plant 9,501

[45] Date of Patent: Apr. 9, 1996

[54] CARNATION PLANT NAMED MONDRIAAN

[75] Inventor: Ronald Schrama, Vinkeveen, Netherlands

[73] Assignee: M. Lek & Zonen B.V., Nieuwveen, Netherlands

[21] Appl. No.: 392,485

[22] Filed: Feb. 23, 1995

[51] Int. Cl.[6] ..... A01H 5/00

[52] U.S. Cl. ..... Plt./70.2

[58] Field of Search ..... Plt./70.1, 70.2, Plt./70.7

*Primary Examiner*—James R. Feyrer

*Attorney, Agent, or Firm*—Foley & Lardner

[57] ABSTRACT

A new and distinct cultivar of carnation plant named Mondriaan, characterized by its dark red main flower color with white margins and darker red throats; upper surfAce of flower is generally flat, generally wavy petal form, with crenate-dentate outer margin; elliptical, flat leaves which are blue-green in color, and it funnel-shaped calyx with short, acute lobes.

2 Drawing Sheets

The present invention comprises a new and distinct cultivar of Carnation, botanically known as *Dianthus caryophyllus* L., and referred to by the cultivar name Mondriaan.

Mondriaan is the product of a planned breeding program carried out in Nieuwveen, The Netherlands.

Mondriaan was originated by the inventor from a hybridization made in Nieuwveen in 1983. The female parent was the cultivar identified as Pico. The male parent was the cultivar identified as ML 553.

Mondriaan was discovered and selected as one flowering plant with the progeny of the stated parentage by the inventor in a controlled environment in Nieuwveen.

The first act of asexual reproduction of Mondriaan was accomplished when vegetative cuttings were taken from the initial selection in July 1984 in a controlled environment in Nieuwveen by or under the supervision of the inventor.

Horitcultural examination of selected units initiated following asexual reproduction has demonstrated that the combination of characteristics as herein disclosed for Mondriaan are firmly fixed and are retained through successive generations of asexual reproduction.

Mondriaan has not been observed under all possible environmental conditions. The phenotype may vary somewhat with variations in environment such as temperature, light intensity and daylength, without, however, any variation in genotype.

The following observations, measurements and comparisons describe plants grown in Wageningen and Nieuwveen, The Netherlands under greenhouse conditions which closely approximate those generally used in commercial practice.

The following traits have been repeatedly observed and are determined to be basic characteristics of Mondriaan which in combination distinguish this carnation as a new and distinct cultivar:

1. The base color of the flowers is a dark red, with the petal throats or bases being a darker red, and the entire margin white.

2. The top surface of the fully opened corolla is generally flat, merging into generally concave sides.

3. Foliage is elliptical in shape, relatively long and narrow, and blue-green in color.

4. Individual flower petals are undulating in cross-section with the margin being crenate-dentate.

5. The calyx is funnel shaped, with the lobes being short and acute in shape and not infused with anthocyanin.

The accompanying color photographic drawings show typical inflorescence and foliage characteristics of Mondriaan.

The photo on sheet 1 illustrates a potted plant of the new cultivar with many open flowers and buds.

The photo on sheet 2 shows various plant parts, including an open flower, individual petals, stems and calyx. Colors are as nearly true as possible with illustrations of this type, although the true base color of the flowers is not precisely shown in either of the photographs.

In the following description, color references are made to the Royal Horticultural Colour Chart. Color values were determined indoors in a north light in Wageningen.

Classification:

*Botanical.*—*Dianthus caryophyllus* L., cv. Mondriaan.

*Commerical.*—Spray/pot carnation.

INFLORESCENCE CHARACTERISTICS

Flowering response: 11–20 weeks after planting rooted cuttings and with one pinch, and depending on season.

Number of buds and flowers per stem: 1–5.

Stem length: 18–22 cm; stems are grooved.

Flower:

*Size.*—Approximately 3.0 cm in diameter.

*Type.*—Double.

*Form.*—Top surface flat, periphery of flower generally concave.

*Buds.*—Cylindrical in shape just before opening.

*Calyx.*—Funnel-shaped; lobes are short and acute in shape, and longitudinal axis convex; not infused with anthocyanin; apex of both outer and inner lobes of epicalyx is acuminate.

*Petals.*—Generally wavy or undulationg in cross-section, margin is crenate-dentate; see photo for petal shape and size.

Color:

*General tonality from a distance of three meters.*—Dark red.

*Upper surface.*—Main color (claw excluded) is dark red 60A; throat or base of petals is a darker red 187A, and the entire margin is white; color fades very little during maturation.

Fragrance: Slight.

Reproductive organs:

*Androecium.*—Present.

*Gynoecium.*—Ovaries are rhomboid-obovoid in shape; main color of lower part is white and color of upper part (tip excluded) is medium green; surface is ribbed; no transformation of ovaries into flower buds; generally 2 styles but occasionally 3; styles do not have a shoulder; color of stigma is white with a purple flush.

PLANT CHARACTERISTICS

Growth habit: Vigorous growth habit.
Branching pattern: 1–5 side branches per stem.
Height: Approximately 28 cm in height at time of flowering.
Stems; Straight and rigid, firmly supporting flowers.

Foliage:

*Shape.*—Elliptical; upper surface is flat in cross-section; longitudinal axis is rolled.

*Texture.*—Glancosity is present, margin is not ciliated.

*Size.*—Length approximately 5.0–7.0 cm; width approximately 0.5 cm.

*Color.*—Typical carnation, blue-green.

It is claimed:

1. A new and distinct cultivar of carnation plant named Mondriaan, as illustrated and described.

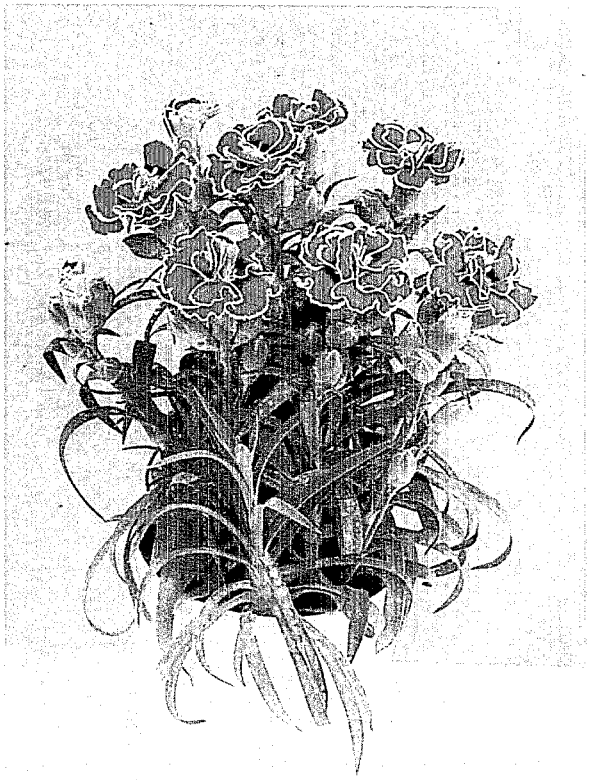

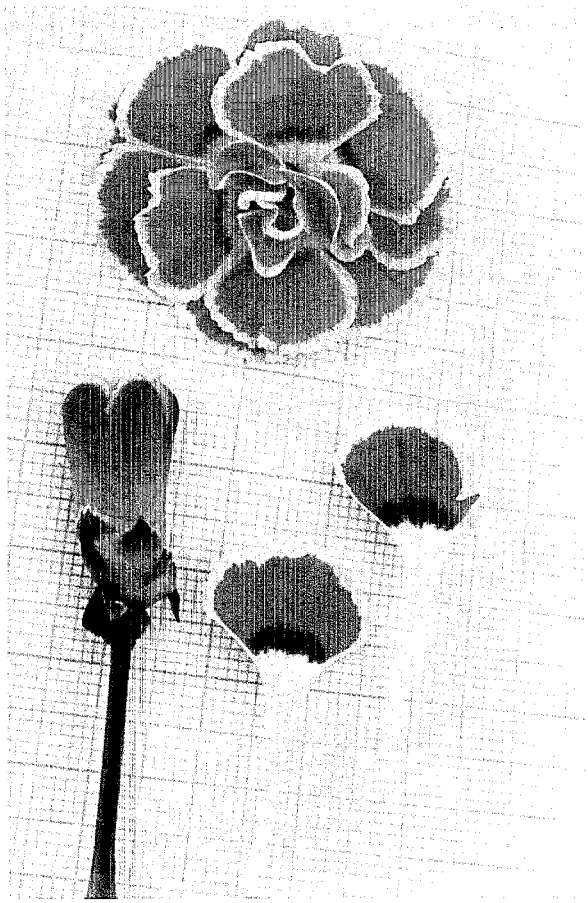

* * * * *